US010398368B2

(12) United States Patent
Yoshida et al.

(10) Patent No.: US 10,398,368 B2
(45) Date of Patent: Sep. 3, 2019

(54) ONBOARD SYSTEM, VEHICLE CONTROL DEVICE, AND PROGRAM PRODUCT FOR VEHICLE CONTROL DEVICE

(71) Applicant: DENSO CORPORATION, Kariya, Aichi-pref. (JP)

(72) Inventors: Ichiro Yoshida, Kariya (JP); Kiyohiko Sawada, Kariya (JP)

(73) Assignee: DENSO CORPORATION, Kariya, Aichi-pref. (JP)

( * ) Notice: Subject to any disclaimer, the term of this patent is extended or adjusted under 35 U.S.C. 154(b) by 332 days.

(21) Appl. No.: 15/513,119

(22) PCT Filed: Sep. 8, 2015

(86) PCT No.: PCT/JP2015/004564
§ 371 (c)(1),
(2) Date: Mar. 21, 2017

(87) PCT Pub. No.: WO2016/047063
PCT Pub. Date: Mar. 31, 2016

(65) Prior Publication Data
US 2017/0303842 A1 Oct. 26, 2017

(30) Foreign Application Priority Data
Sep. 25, 2014 (JP) .................. 2014-195494

(51) Int. Cl.
A61B 5/18 (2006.01)
A61B 5/0476 (2006.01)
(Continued)

(52) U.S. Cl.
CPC .............. A61B 5/18 (2013.01); A61B 5/0476 (2013.01); A61B 5/6893 (2013.01);
(Continued)

(58) Field of Classification Search
None
See application file for complete search history.

(56) References Cited

U.S. PATENT DOCUMENTS

2013/0070043 A1* 3/2013 Geva .................... B60K 28/066
348/14.02
2014/0039757 A1* 2/2014 Prakah-Asante ......... G06F 7/00
701/36
(Continued)

FOREIGN PATENT DOCUMENTS

JP H9-86223 A 3/1997
JP 2001-219760 A 8/2001
(Continued)

Primary Examiner — David P. Merlino
(74) Attorney, Agent, or Firm — Knobbe, Martens, Olson & Bear, LLP

(57) ABSTRACT

An onboard system equipped to a vehicle includes a vehicle control device controlling a switching of a driving mode of the vehicle between a manual driving and a self-driving, and a brain activity sensor capable of detecting an activated portion of a brain of a driver of the vehicle. The vehicle control device determines whether a degree of uneasiness felt by the driver exceeds a threshold or not based on a detection result detected by the brain activity sensor before the switching of the driving mode. When determining that the degree of uneasiness felt by the driver does not exceed the threshold, the vehicle control device switches the driving mode. When determining that the degree of uneasiness felt by the driver exceeds the threshold, the vehicle control device performs a vehicle control corresponding to the degree of uneasiness felt by the driver.

15 Claims, 9 Drawing Sheets

(51) Int. Cl.
*B60W 50/10* (2012.01)
*B60W 50/14* (2012.01)
*B60W 30/182* (2012.01)
*B60W 40/08* (2012.01)
*A61B 5/00* (2006.01)
*B60W 50/00* (2006.01)

(52) U.S. Cl.
CPC .......... *B60W 30/182* (2013.01); *B60W 40/08* (2013.01); *B60W 50/0097* (2013.01); *B60W 50/0098* (2013.01); *B60W 50/10* (2013.01); *B60W 50/14* (2013.01); *B60W 2040/0872* (2013.01); *B60W 2050/0095* (2013.01); *B60W 2050/146* (2013.01); *B60W 2540/22* (2013.01); *B60W 2540/26* (2013.01); *B60W 2550/402* (2013.01)

(56) References Cited

U.S. PATENT DOCUMENTS

| | | | |
|---|---|---|---|
| 2014/0148988 A1* | 5/2014 | Lathrop | B60W 50/10 701/23 |
| 2015/0246673 A1* | 9/2015 | Tseng | B60W 30/00 701/23 |

FOREIGN PATENT DOCUMENTS

| | | |
|---|---|---|
| JP | 2011-87784 A | 5/2011 |
| JP | 2012-173803 A | 9/2012 |
| JP | 2014-108771 A | 6/2014 |

* cited by examiner

ONBOARD SYSTEM, VEHICLE CONTROL DEVICE, AND PROGRAM PRODUCT FOR VEHICLE CONTROL DEVICE

CROSS REFERENCE TO RELATED APPLICATION

This application is based on Japanese Patent Application No. 2014-195494 filed on Sep. 25, 2014, the disclosure of which is incorporated herein by reference.

TECHNICAL FIELD

The present disclosure relates to an onboard system, a vehicle control device, and a program product for the vehicle control device.

BACKGROUND ART

Conventionally, as a known technology, at the time of switching from self-driving to manual driving, an attentiveness of a driver is detected, and the switching operation is performed according to the detected attentiveness of the driver.

PRIOR ART LITERATURE

Patent Literature

[Patent Literature 1] JP 2001-219760 A

SUMMARY OF INVENTION

However, according to the inventors' study, an attentiveness of the driver is not the only factor that affects the switching of the driving mode. When the self-driving is in actually activated state and a driving manner of the self-driving is different from a driving manner of the driver's manual driving, the driver who is not familiar with the self-driving may feel uneasy about the self-travelling of the vehicle. For example, when the self-driving is being performed in a manner substantially different from a driver's manual driving manner immediately before switching from the self-driving to the manual driving, the driver may feel uneasy in taking over the self-driving.

In view of the above-mentioned difficulties, it is an object of the present disclosure to provide an onboard system, a vehicle control device, and a program product for the vehicle control device, each of which is capable of coping with a driver's uneasiness when switching a driving mode.

According to an aspect of the present disclosure, an onboard system equipped to a vehicle includes a vehicle control device controlling a switching of a driving mode of the vehicle between a manual driving and a self-driving, and a brain activity sensor capable of detecting an activated portion of a brain of a driver of the vehicle. The vehicle control device determines whether a degree of uneasiness felt by the driver exceeds a threshold or not based on a detection result detected by the brain activity sensor before the switching of the driving mode. When determining that the degree of uneasiness felt by the driver does not exceed the threshold, the vehicle control device switches the driving mode. When determining that the degree of uneasiness felt by the driver exceeds the threshold, the vehicle control device performs a vehicle control corresponding to the degree of uneasiness felt by the driver.

As described above, the onboard system determines whether the degree of driver's uneasiness exceeds a threshold or not, with the use of the detection result of the brain activity sensor that can detect an activated portion of the driver's brain. When it is determined that the degree of driver's uneasiness exceeds the threshold, the vehicle is controlled to cope with the high degree of driver's uneasiness. Thus, the vehicle control corresponding to the driver's uneasiness can be performed at the switching time of the driving mode.

According to another aspect of the present disclosure, a program product stored in a computer-readable non-transitory tangible storage medium includes instructions to be executed by a computer. The program product is used for a vehicle control device for controlling a switching of a driving mode of a vehicle between a manual driving and a self-driving. The instructions include determining whether a degree of uneasiness felt by a driver of the vehicle exceeds a threshold or not based on a detection result of a brain activity sensor, wherein the brain activity sensor is capable of detecting an activated portion of a brain of the driver of the vehicle before the switching of the driving mode, switching the driving mode when determining that the degree of uneasiness felt by the driver does not exceed the threshold, and performing a vehicle control corresponding to the degree of uneasiness felt by the driver when determining that the degree of uneasiness felt by the driver exceeds the threshold.

Similarly, in the above program product, the vehicle control that copes with the driver's uneasiness can be performed at the switching time of the driving mode.

BRIEF DESCRIPTION OF DRAWINGS

The above and other objects, features and advantages of the present invention will become more apparent from the following detailed description made with reference to the accompanying drawings. In the drawings.

EMBODIMENTS FOR CARRYING OUT INVENTION

Figure 1:
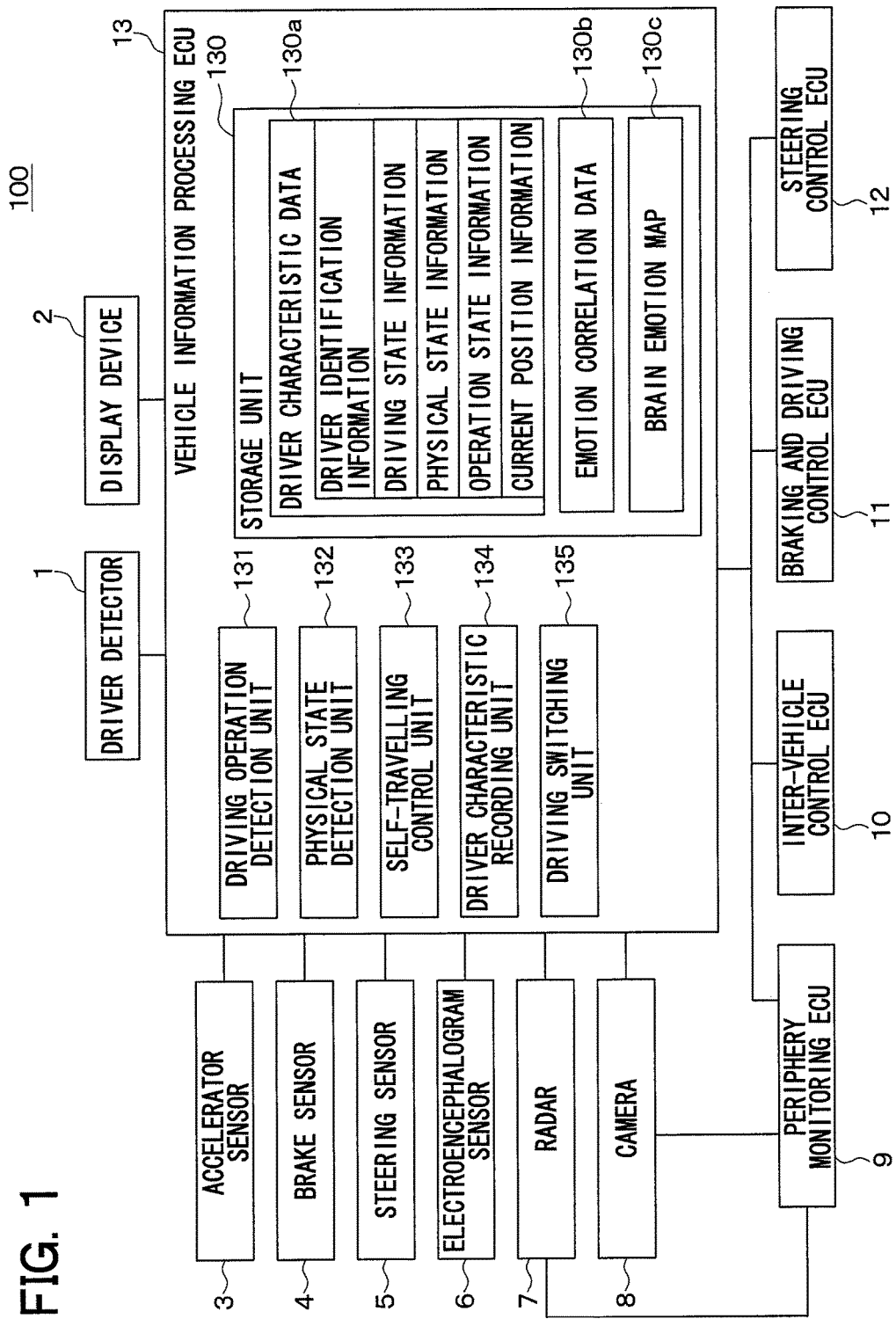
FIG. 1 is a block diagram of an onboard system according to an embodiment of the present disclosure.

Hereinafter, a description will be given of an embodiment of the present disclosure. As illustrated in FIG. 1, an onboard system equipped to a vehicle according to the present embodiment includes a driver detector 1, a display device 2, an accelerator sensor 3, a brake sensor 4, a steering sensor 5, electroencephalogram sensors 6, a radar 7, a camera 8, a periphery monitoring ECU 9, an inter-vehicle control ECU 10, a braking and driving control ECU 11, a steering control ECU 12, and a vehicle information processing ECU 13. In the present disclosure, the vehicle information processing ECU 13 corresponds to a vehicle control device, and the electroencephalogram sensor 6 corresponds to a brain activity sensor.

The vehicle information processing ECU 13 includes a storage unit 130 that stores data. The vehicle information processing ECU 13 includes a driving state detection unit 131, a physical state detection unit 132, a self-travelling control unit 133, a driver characteristic recording unit 134, and a driving switching unit 135. Those units 131 to 135 may be realized by respective separate microcomputers or special purpose integrated circuits (IC), or may be realized by controlling one microcomputer to execute a program for defining functions of those units 131 to 135.

The driver detector 1 is a device that identifies a driver of a vehicle. The driver detector 1 may be a device that communicates with a mobile device such as an electronic key carried by the driver to acquire a specific device ID included in the mobile device, and identifies the driver corresponding to the acquired device ID with reference to a database associating multiple device IDs with multiple drivers in one-to-one manner. Alternatively, the driver detector 1 may be a device that images a face of the driver to acquire a face image, and specifies the driver corresponding to the acquired face image with reference to a database associating multiple face images with multiple drivers in one-to-one manner.

The database may be stored in a memory included in the driver detector 1. Alternatively, the database may be stored in a center server disposed outside of the vehicle, and the driver detector 1 may communicate with the center server, and refer to the database in the center server. In the latter case, since a falsification possibility of the database is low, the security is enhanced.

The display device 2 is a device that displays an image so that the driver of the vehicle can view the image. The image displayed on the display device 2 is, for example, an image around the vehicle which is captured by the camera 8.

The accelerator sensor 3 is a device that detects the operation amount of an accelerator pedal by the driver. For example, the accelerator sensor 3 can be realized by an angular sensor attached to the accelerator pedal. The brake sensor 4 is a device that detects the operation amount of a brake pedal by the driver, and can be realized by, for example, an angular sensor attached to the brake pedal. The steering sensor 5 is a device that detects the operation amount of a steering wheel (rotation angle of a steering wheel) by the driver, and can be realized by, for example, an angular sensor attached to a shaft of the steering wheel.

Detection signals output by those sensors 3, 4, and 5 are input to the vehicle information processing ECU 13, and the driving state detection unit 131 detects the content of the driving operation made by the driver on the basis of the detection signals from those sensors 3, 4, and 5. In addition, the driving state detection unit 131 may detect the content of the driving operation made by the driver based on detection signals from a sensor that detects the operation of changing a gear position of the vehicle, a sensor that detects the operation of turning on and off a power supply of the vehicle and so on, in addition to the above-described sensors 3, 4, and 5.

The electroencephalogram sensors 6 are known sensors for detecting electroencephalograms of the driver. The electroencephalogram sensors 6 are disposed at multiple positions in the vicinity of a surface of a driver's head, and simultaneously detect the electroencephalograms at the multiple positions. Alternatively, the electroencephalogram sensors 6 may be contact with the surface of the head at the multiple positions using a wearable appliance (for example, a helmet) for applying a preset pressure to the electroencephalogram sensors 6, and simultaneously detect the electroencephalograms at the multiple positions.

In addition, although not illustrated, a biological information sensor that is attached to a steering wheel for detecting biological information on the driver such as an electrocardiogram, a heart rate, a blood pressure, muscle action (myoelectric potential), or the amount of perspiration may be included in an onboard system 100. The biological information sensor may also be a wearable sensor attached to clothing or hair accessories of the driver.

The detection signals output from the electroencephalogram sensors 6 and the biological information sensor are input to the vehicle information processing ECU 13. The physical state detection unit 132 measures a distribution of active areas (distribution of activated portions) of a brain on the basis of detection signals from the electroencephalogram sensors 6. The physical state detection unit 132 detects the degree of driver's uneasiness and the like on the basis of the measurement result and detection signals output from the biological information sensor, and outputs the detected degree of driver's uneasiness and the like as physical state information. The physical state information includes the distribution of the active areas of the driver's brain, the electrocardiogram, the heart rate, the blood pressure, the muscle action (myoelectric potential), the amount of perspiration, and so on.

The following will describe the degree of uneasiness. The brain includes a portion for processing an instinctive reaction and a portion for processing a rational reaction. Because a portion that reacts to pleasure and a portion reacts to uneasiness are different from each other in the brain, what kind of emotion the person has can be detected by detection of the activated portion of the brain with the use of the electroencephalogram sensors for detecting the electroencephalograms at the multiple positions of the brain.

Figure 2A:
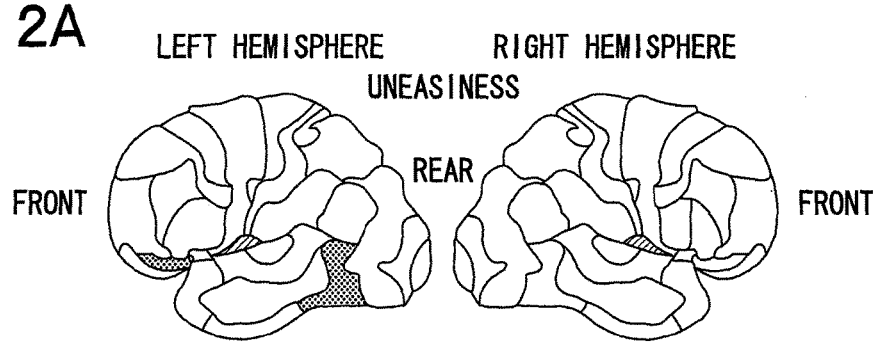
FIG. 2A is a diagram illustrating a relation between a distribution of active areas of a brain and an uneasiness emotion of a person.
Figure 2B:
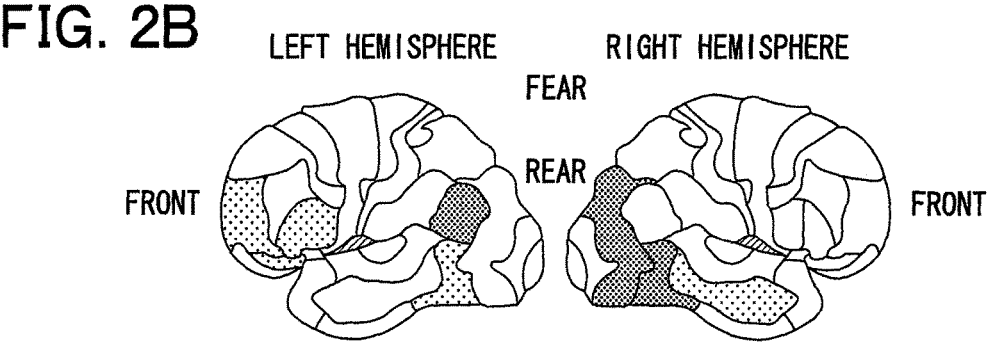
FIG. 2B is a diagram illustrating a relation between a distribution of active areas of a brain and a fear emotion of a person.
Figure 2C:
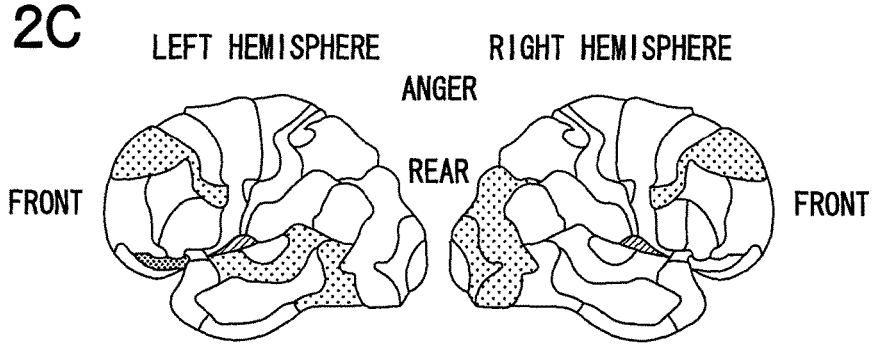
FIG. 2C is a diagram illustrating a relation between a distribution of active areas of a brain and an angry emotion of a person.
Figure 2D:
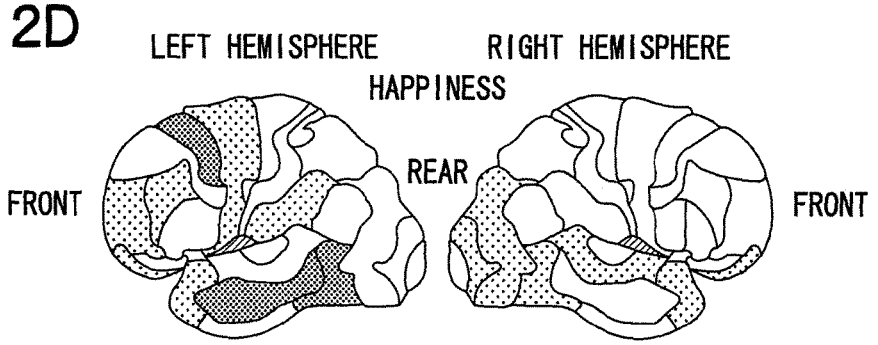
FIG. 2D is a diagram illustrating a relation between a distribution of active areas of a brain and a happy emotion of a person.

FIGS. 2A to 2D illustrate relations between the distribution of the active areas of the brain and the person's emotion in the Brodmann's brain map. FIGS. 2A, 2B, 2C, and 2D illustrate the distributions of the active areas of the brain corresponding to uneasiness, fear, anger, and happiness, respectively. The density of dots in dotted pattern increases with an increase of the activation level. Brains in FIGS. 2A and 2B show a state in which the uneasiness occurs, and brains of FIGS. 2C and 2D show a state in which the uneasiness do not occur.

A developer of the onboard system 100 specifies, through experiments, a relation between the degree of driver's uneasiness obtained from conversation contents and voice and the degree of driver's uneasiness obtained from activated portions of the brain. The developer of the onboard system 100 creates a brain emotion map 130c indicative of a relation between the distribution of the activated portions of the brain and the degree of driver's uneasiness on the basis of the result specified by the experiments. The created brain emotion map 130c is stored in the storage unit 130 at the time of manufacturing the vehicle information processing ECU 13. The physical state detection unit 132 applies the time-varying distribution of the activated portions of the brain acquired by the electroencephalogram sensors 6 to the brain emotion map 130c, thereby being capable of specifying the degree of driver's uneasiness at corresponding time. When specifying the degree of uneasiness, in addition to the measurement result of the distribution of the active areas of the brain, the level of the electrocardiogram, the heart rate, the blood pressure, the muscle action (myoelectric potential), and the amount of perspiration may be adjunctively used.

The radar 7 is a device that detects a distance and a direction to an object such as another vehicle or a pedestrian around the vehicle with the use of microwaves or laser, and the detection signal is input to the vehicle information processing ECU 13 and the periphery monitoring ECU 9. The camera 8 images an external situation of the vehicle, and data of the captured image is input to the vehicle information processing ECU 13 and the periphery monitoring ECU 9.

The periphery monitoring ECU 9 specifies surrounding situation of the vehicle (what object is present on which position) on the basis of the input information (image, distance and direction to the object) input from the radar 7 and the camera 8, and controls the vehicle so that the vehicle does not collide with the object. In order to achieve the above purpose, the periphery monitoring ECU 9 outputs commands to the inter-vehicle control ECU 10 and the braking and driving control ECU 11.

The braking and driving control ECU 11 is a device that controls the operation of a vehicle braking device, a motor used for traveling, an engine, and so on according to the commands received from the periphery monitoring ECU 9 and the vehicle information processing ECU 13. The braking and driving control ECU 11 controls a travelling (braking or acceleration) in an anteroposterior direction of the vehicle. The steering control ECU 12 controls a steering angle of the steering wheel of the vehicle according to the commands received from the periphery monitoring ECU 9 and the vehicle information processing ECU 13, to thereby control a left or right moving direction of the vehicle.

Although not illustrated, the onboard system 100 has a GPS receiver and so on, and the vehicle information processing ECU 13 measures a current position of the subject vehicle represented by latitude and longitude information on the basis of position information output from the GPS receiver.

In addition, the self-travelling control unit 133 specifies the surrounding situation of the vehicle (what object is present on which position) on the basis of the information (image, distance and direction to the object) input from the radar 7 and the camera 8, and controls the self-driving (steering, driving, braking) of the vehicle on the basis of the specified information without depending on the driver's operation. In order to achieve the above, the self-travelling control unit 133 outputs commands to the inter-vehicle control ECU 10, the braking and driving control ECU 11, and the steering control ECU 12. The self-travelling control unit 133 according to the present embodiment operates only when the driving switching unit 135 switches the driving mode to the self-driving. Incidentally, when the driving switching unit 135 switches the driving mode to the manual driving, the self-travelling control unit 133 is deactivated, and the vehicle information processing ECU 13 outputs the commands to the braking and driving control ECU 11 and the steering control ECU 12 according to the operation made by the driver on the accelerator pedal, on the brake pedal, and on the steering wheel.

Since the details of the control contents of the self-travelling control unit 133 is well known, a detailed description will be omitted. In some cases, the self-travelling control unit 133 may determine a road environment in which a road situation where the vehicle will travel in the future is difficult to be specified by the camera 8 or the radar 7. In this case, the self-travelling control unit 133 cannot grasp the road situation. For example, there is a case in which a change rate of a road shape is substantially large, a forward road shape is hidden by trees positioned along the roadside, or a case in which buildings cause a poor forward view. Whether such a situation is present or not can be determined according to the information output from the radar 7 and the camera 8.

In the above-described case, the self-travelling control unit 133 performs a preliminary determination on the basis of the captured image data output from the camera 8 and a known map database or road shape database stored in the storage unit 130. In the preliminary determination, what is present at a position that cannot be imaged by the camera 8 or a position that is not viewed from the driver is predicted on the basis of the map database or the road shape database. What kind of cruise control (acceleration and deceleration, steering operation, and so on) is required in order to travel safely is determined, and the commands are output to the inter-vehicle control ECU 10 and the braking and driving control ECU 11 so as to realize the determined cruise control. In order to ensure the safety of the driver as described above, the operation for performing a preparation to which the self-driving can contribute is referred to as "defense self-driving".

The driver characteristic recording unit 134 sequentially stores identification information on the driver detected by the driver detector 1, driving state information detected by the driving state detection unit 131, the physical state information output from the physical state detection unit 132, operation state information of the self-travelling control unit 133, and current position information on the subject vehicle as driver characteristic data 130a in the storage unit 130. The operation state information of the self-travelling control unit 133 is information on whether the self-driving is performed or not. As a result, the driver characteristic data 130a indicative of how the driver reacts in response to a position and a kind of traveling state the vehicle travels is accumulated in the storage unit 130. In a period when the driver performs characteristic operation or reaction, the driver characteristic data 130a in the above period may be transmitted to the center server outside the vehicle with the use of a communication device, which is not illustrated.

The above-mentioned road shape data includes information indicating a self-driving category of each road. The self-driving category is information indicating that the road corresponds to which category defined with consideration that whether the self-driving or the manual driving is enabled or not. The category may be one of a self-driving dedicated road, a self-driving priority road, a manual driving dedicated road, or a special self-driving road. In this example, the self-driving dedicated road is a road which permits only the self-driving. The self-driving priority road is a road where the self-driving is recommended although both of the manual driving and the self-driving are permitted. The manual driving dedicated road is a road which permits only the manual driving. The special self-driving road is a road where the self-driving is permitted for only vehicles having a performance in which a self-driving precision (performance) is equal to or higher than a preset level.

The driving switching unit 135 of the vehicle information processing ECU 13 performs switching of driving mode, that is, the operation related to switching between the self-driving and the manual driving. The vehicle information processing ECU 13 adds the self-driving categories of the roads around the subject vehicle to a map to be displayed on the display device 2, and displays the map to the driver. At the same time, the driving switching unit 135 performs the operation using information on a recommended route to a destination designated by a navigation apparatus (not illustrated) equipped in the same vehicle. Specifically, the driving switching unit 135 determines whether the switching from the self-driving to the manual driving is required within a predetermined time or not, on the basis of the information on the recommended route and the self-driving categories. When it is determined that the switching is required, the driver is notified of a fact that the manual driving is required with the use of the display device 2, a sound generation device (not illustrated), a vibration actuator (not illustrated) that vibrates a driver's seat or the like.

In addition, whether the effect of the notification to the driver is obtained or not, is determined by a driver response detector (not illustrated) which detects whether the driver responds to the notification or not, and the notification is continued until attention is surely notified to the driver. A driver situation determinator may be realized by, for example, a switch operable by the driver.

When a response from the driver to the notification made for the driver is absent within a predetermined waiting time, the driving switching unit 135 calls attention of the driver by giving a stimulus which activates the driver's conscious (brain) to the driver. Such a stimulus is performed by using an actuator (not illustrated) for causing the driver to conceive sounds, vibration, or a weak current. Such an actuator may be attached to the steering wheel, or may be realized as a wearable device.

In addition, when switching the driving mode from the manual driving to the self-driving and when switching the driving mode from the self-driving to the manual driving, in order to ensure the safety of the driver and the occupant, the driving switching unit 135 performs the notification in the form corresponding to the driver's characteristic (personality, excise capacity, etc.). Specifically, notification time, a magnitude of notification sound, a notification procedure and so on may be set according to the current driver. The current driver can be specified on the basis of an output from the driver detector 1. The information on what kinds of notification is performed for which driver may be recorded in, for example, the storage unit 130 in advance.

Alternatively, on what kind of form the notification is performed may be determined on the basis of the driver characteristic data 130*a*. For example, a mean value of depression speeds of the brake pedal by the current driver is determined on the basis of the driver characteristic data 130*a*. With an increase of the mean value of the depression speeds (that is, the driver relatively slow in the perception of a risk), the notification may be carried out at an earlier time.

A basic configuration of the onboard system 100 according to the present embodiment is described above. When the vehicle automatically switches from the self-driving to the manual driving, or switches from the manual driving to the self-driving, the driver (or occupant) may feel uneasy depending on the traveling state of the vehicle (that is, how the vehicle travels according to the environment). Under this circumstance, the driver characteristic recording unit 134 according to the present embodiment stores emotion correlation data 130*b* indicative of a correlation between the traveling state of the vehicle and the degree of driver's (or occupant's) uneasiness in the storage unit 130. The emotion correlation data 130*b* is information indicative of in what traveling state the driver (or occupant) is likely to feel uneasy. The emotion correlation data 130*b* includes at least position information on a point at which the degree of uneasiness of the driver reaches a predetermined level or more.

The operation of the driver characteristic recording unit 134 for recording such emotion correlation data 130*b* will be described in detail.

First, as has been already described, the driver characteristic recording unit 134 sequentially stores the driver identification information, the driving state information, the physical state information, the operation state information of the self-travelling control unit 133, and the current position information as the driver characteristic information in the storage unit 130 in bulk.

The driving state information includes, specifically, information (1) to (18) described below. The following pieces of data affect the travel, and the driver may feel that the vehicle travels safely, or travels unstably, according to values of the following pieces of data.

(1) Time when start operation (for example, main power-on operation) is performed.

(2) Time when main power stop operation is performed.

(3) Duration since the main power of the vehicle turns on until the operation of the vehicle starts (for example, engine start).

(4) Information on stability of the vehicle when the travel starts. When unstable control operation first occurs particularly in the self-driving, uneasy emotion of the driver about the vehicle may be increased. Thus, the information on the stability is helpful. As a data value of the stability, for example, a reciprocal of a variation (for example, standard deviation) of a longitudinal acceleration or a lateral acceleration of the vehicle may be employed. In that case, with an increase of the data value, the stability becomes higher. In the self-driving, the degree of user's uneasiness increases in response to an abnormal operation (unnecessary vibration or sound occurs).

(5) Time-varying content of gear change (for example, forward, backward). In the manual operation, the degree of user's uneasiness increases with a failure of a gear change.

(6) Time-varying content of accelerator operation and actual acceleration of the vehicle, or time-varying content of braking operation and actual deceleration of the vehicle. An accelerator response of the vehicle can be specified by time-varying content of the accelerator operation and the actual acceleration of the vehicle. A brake response of the vehicle can be specified by time-varying content of the braking operation and the actual deceleration of the vehicle.

(7) Time-varying content of the operation of the steering wheel and the actual lateral acceleration of the vehicle.

(8) Time-varying content of an inter-vehicle distance to a preceding vehicle. Information on the inter-vehicle distance is specified on the basis of output results from the radar 7 and the camera 8.

In the above respective items (4) to (8), the driver or the occupant may feel uneasy when the operation content is performed in different manner from his favorable content (driving content usually performed by the driver).

(9) Time-varying operation state of a travel stabilization control device (stabilizer), which is not illustrated. When the vibration of a vehicle body is not suppressed, the driver or the occupant may feel uneasy.

(10) Time-varying state of vehicle height. Since a breadth of visibility and the ease of confirming a situation in the vicinity of the vehicle increase driver's sense of ease, such time-varying height information related to the vehicle is recorded.

(11) Power on state or power off state of an illumination lamp of the vehicle, and state of time-varying optical axis direction control. When a visibility performance in the night is degraded, the degree of user's uneasiness is increased.

(12) Time-varying state of display mode (blind spot display, bird's eye display, etc.) in which the display device 2 displays an image captured by the camera 8. Such information is necessary for the driver or the occupant to determine the safety during the driving.

(13) Time-varying state of a volume of an audio device (not illustrated). Some driver may become uncomfortable depending on a volume and the magnitude of high frequency sound or low frequency sound.

(14) Time-varying state of the arrangement and posture of seats. Some driver may have a request for changing an angle of a backrest to improve visibility during driving and to relax during a break time.

(15) Time-varying state of wiper operation. When the visibility is poor under rainy weather, the driver may feel uneasy about the execution of the manual driving.

(16) Time-varying state of door lock operation. Some occupant may worry about whether the door lock is surely carried out. When the driver is not sure about the door lock, the driver may feel uneasy.

(17) Time-varying state of window operation of door. When a window glass cannot be controlled to be opened or closed to a designated position, the driver may feel uneasy.

(18) Controlled variable of various ECUs (inter-vehicle control ECU 10, braking and driving control ECU 11, steering control ECU 12, etc.).

The above items (13) to (17) are information on factors which may affect the driver.

In addition to the above items (1) to (18), the driving state information may further include time-varying information on the characteristics of a road on which the vehicle travels. The information on the characteristics of the road includes information such as the radius of curvature of a curve of the road, a gradient, road surface conditions (for example, a material and a friction coefficient of a road surface), a road width, number of lanes, a congestion degree, and weather. The radius of curvature of the road, the gradient, the road surface conditions (for example, whether the road is paved or not), the road width, and the number of lanes are identified with the use of the information recorded in the road shape data in advance. In addition, the congestion degree and the weather are identified with the use of road traffic information and weather information received from a transmission device (for example, VICS (VICS is a registered trademark) beacon) outside the vehicle.

Incidentally, as a method of recording the driver characteristic information using the driver characteristic recording unit 134, a record captured for a period of a set time (for example, 10 minutes) dating from the present time to the past time may be held in a driving recorder. The driving recorder is an imaging device which captures and records a view outside of the vehicle using a camera.

The driver characteristic information captured during the past set time period is always stored in the storage unit 130, and the driver characteristic information before the past set time period may be stored in a memory of a mobile device that can communicate with the storage unit 130 and the onboard system 100, or may be stored in a storage medium of a server outside of the vehicle for a predetermined duration after a condition required for recording to be described later is satisfied so far as the condition is satisfied.

The condition required for recoding may include a condition in which any detection value of, for example, bio-sensing items of the driver (the level of electroencephalograms, the level of the electrocardiogram, the heart rate, the blood pressure, the muscle action (myoelectric potential), and the amount of perspiration) becomes more than a reference value. In that case, when the condition required for recording is satisfied, the driver characteristics recording unit 134 stores, in the storage unit 130, the driver characteristic information from a time when the reaction amount is increased to a time going back for the set time period in the past as information immediately before abnormality.

In addition, as the condition required for recording, for example, there is a case in which an acceleration sensor of the vehicle detects acceleration becomes equal to or more than a predetermined value. In that case, the predetermined duration may be a time period until the electroencephalogram level detected by the electroencephalogram sensors 6 returns to a normal level.

It is assumed that after a normal state is changed to a state in which any detection value of the bio-sensing items of the driver becomes more than the above-mentioned reference value, the state is returned to the normal state (for example, a state in which the detection value is less than the reference value). In that case, the driver characteristic recording unit 134 stores, in the storage unit 130, the driver characteristic information during a period from a time when the detection value becomes larger than the reference value to a time when the state returns to the normal state as information immediately after the abnormality.

The driver characteristic recording unit 134 accumulates such data to accumulate information on what kind of movement (travel) of the vehicle causes how much the user feels uneasy.

In addition, the driver characteristic recording unit 134 uses the above-mentioned driver characteristic information in order to create the above-mentioned emotion correlation data 130b. Specifically, the degree of time-varying driver's uneasiness is specified at each past time for each driver with the use of the identification information and the physical state information of the corresponding driver.

Further, the driver characteristic recording unit 134 classifies the traveling states at that time into multiple traveling state categories at each past time for each driver with the use of the identification information on the driver, the driving state information, the operation state information on the self-travelling control unit 133, and the current position information. In this example, all of the information in the identification information on the driver, the driving state information, the operation state information of the self-travelling control unit 133, and the current position information are parameters indicative of the traveling state. The traveling states belonging to the same traveling state category are classified so that the degree of similarity to the traveling state which is a reference of the traveling state category becomes higher than a reference value. As a method of calculating the degree of similarity between two traveling states, a known method (for example, template matching or the like) of calculating the degree of similarity between the respective quantities having multiple parameters is employed. For example, the degree of similarity between the traveling states at the same point is high. For example, even not at the same point, the degree of similarity between the traveling states at points where the width, the radius of curvature, or the like is the same is high. As a result, the traveling state category at each past time for each driver is specified.

The driver characteristic recording unit 134 associates the degree of uneasiness with the traveling state category at each past time for each driver as described above to calculate a representative value (for example, mean value, median) of the degree of uneasiness in each traveling state category for each driver. The driver characteristic recording unit 134 stores the calculated representative value as the emotion correlation data 130b in the storage unit 130.

With the use of the emotion correlation data 130b described above, it is possible to predict what consciousness and emotion the user may have with respect to a position and a manner of driving operation that is performed at the position. When the same reaction occurs in the same traveling state category successively by multiple times, the reliability of that data becomes higher.

The following will describe the operation of the occupant support using the emotion correlation data 130b recorded as described above. The driving switching unit 135 estimates a state (the degree of uneasiness) of the driver when switching the driving mode, on the basis of the traveling state category to which the current traveling state belongs and the emotion correlation data 130b. The driving switching unit 135 switches the driving mode when the driver does not feel uneasy and the driving mode is switchable safely.

First, the operation performed by the driving switching unit 135 during the self-driving of the vehicle will be described with reference to FIG. 3. During the self-driving, first in S110, the driving switching unit 135 specifies the current position of the subject vehicle. Subsequently, in S115, it is determined whether a driving mode switching position from the self-driving mode to the manual driving mode falls within a predetermined distance (for example, 5 km) along the recommended route in a traveling direction. That is, it is determined whether the subject vehicle is approaching a driving mode switching position within the predetermined distance.

The driving switching unit 135 specifies the driving mode switching position on the basis of the information on the above-mentioned self-driving category in the road shape data. For example, a boundary point between the self-driving dedicated road and the manual driving dedicated road may be defined as the driving mode switching position from the self-driving mode to the manual driving mode. For example, a boundary point between the self-driving dedicated road and the self-driving priority road may be defined as the driving mode switching position from the self-driving mode to the manual driving mode. The driving switching unit 135 may receive the driving mode switching position information from a transmission device disposed outside of the vehicle, and specify the driving mode switching position on the basis of the received driving mode switching position information. Alternatively, the driving switching unit 135 may specify the driving mode switching position on the basis of the driving mode switching position information recorded in the storage unit 130. In this case, the driving mode switching position information is information manually set by the user of the vehicle in advance.

In the switching from the self-driving to the manual driving, the various vehicle-mounted devices, which have been automatically controlled by the vehicle, are changed to be entrusted to the person's operation. For that reason, the person needs to pay attention to a fact that the manual driving of the vehicle needs to be performed without any delay when the self-driving is stopped.

Until it is determined that the vehicle approaches the driving mode switching position within the predetermined distance in S115, the process in S110 and S115 is repeated. When it is determined that the vehicle approaches the driving mode switching position within the predetermined distance, the process proceeds to S120.

In S120, the driver is notified of the fact that the vehicle approaches the driving mode switching position by the display device 2, and the driver is asked whether to switch to the manual driving or not by the display device 2.

Figure 4:
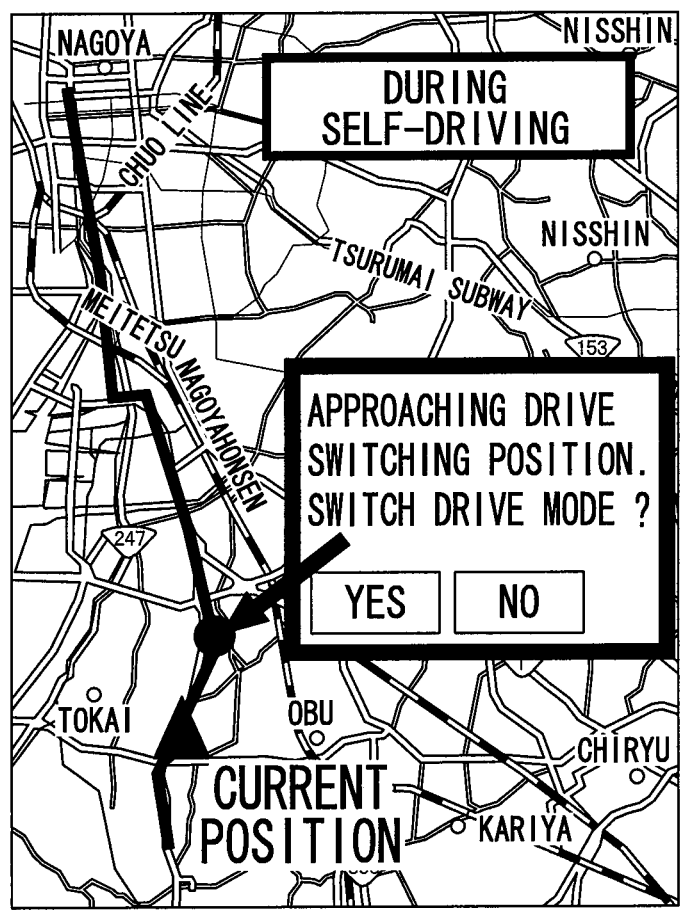
FIG. 4 is a diagram illustrating a message inquiring whether to switch to a manual driving or not.

For example, as illustrated in FIG. 4, the current position, the recommended route, and the driving mode switching position are superimposed on the map, and the image on which a message indicating that the vehicle is in the self-driving, and approaches the driving mode switching position is further superimposed is displayed on the display device 2. Further, as illustrated in FIG. 4, a message inquiring about whether to switch the driving mode or not, is superimposed on the map and is displayed on the display device 2. In response to the inquiry, the driver operates an operation device (for example, touch panel, button) which is not illustrated, or the like to answer whether to switch the driving mode or not.

Subsequently, in S125, it is determined whether the driver's answer to the inquiry in S120 is to switch the driving mode or not to switch the driving mode. When it is determined that the answer is to switch the driving mode, the process proceeds to S130, and when it is determined that the answer is not to switch the driving mode, the process proceeds to S170.

In S130, the manual driving calibration is executed. In the manual driving calibration, it is determined whether the driver is able to perform the manual driving or not, on the basis of the degree of driver's uneasiness, or the like. The details of the manual driving calibration will be described later. Subsequently, in S135, it is determined whether the driver is able to perform the manual driving or not on the basis of the result of the manual driving calibration, and when the driver is able to perform the manual driving, the process proceeds to S140. When it is determined that the driver cannot perform the manual driving, the process proceeds to S175.

In S140, a driving mode switching notification is performed. Specifically, a notification that the driving mode is switched to the manual driving at the driving mode switching position is performed with the use of the display device 2. Subsequently, in S145, it is determined whether driver's approval operation for the notification in S140 is performed on the operation device which is not illustrated. When it is determined that the approval operation is performed, the process proceeds to S150, and when it is determined that the approval operation is not performed, the process proceeds to S155.

Figure 5:
FIG. 5 is a diagram illustrating a message indicative of switching from the self-driving to the manual driving.

In S150, at a time when the vehicle arrives at the driving mode switching position, or at a time a little earlier than the arrival time (for example, 10 seconds ago), a manual/self driving switching control is performed. In other words, the vehicle is switched from the self-driving to the manual driving. In this situation, as illustrated in FIG. 5, a message indicating that the driving mode is switched from the self-driving to the manual driving is superimposed on the map, and displayed on the display device 2. After S150, the process in FIG. 3 is ended.

In S155, it is determined whether the current driving mode (that is, the self-driving) can be continued or not, after passing the driving mode switching position along the recommended route. For example, when the self-driving category of the road after passing the driving mode switching position along the recommended route is the self-driving priority road, it is determined that the current driving mode can be continued, and the process proceeds to S160. For example, when the self-driving category of the road after passing the driving mode switching position along the recommended route is the manual driving dedicated road, it is determined that the current driving mode cannot be continued, and the process proceeds to S165.

In S160, it is determined whether an elapsed time after the notification is performed in S140 reaches a predetermined waiting time (for example, 1 minute). When the elapsed time does not reach the predetermined waiting time, the process returns to S145. When the elapsed time reaches the predetermined waiting time, the process returns to S110 while the self-driving is continued.

Figure 6:
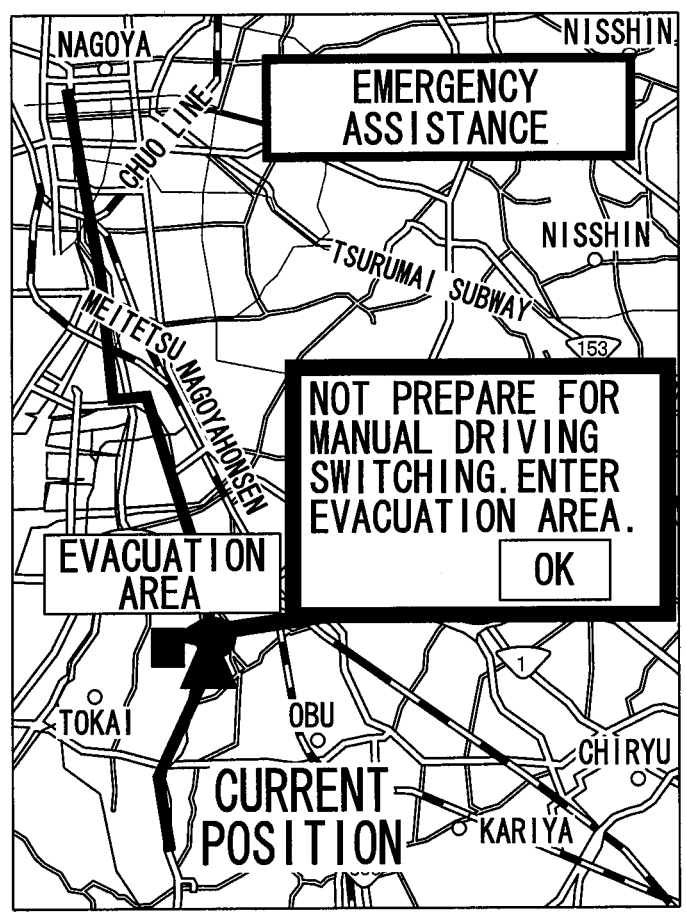
FIG. 6 is a diagram illustrating an error message during an urgent process.

In S165, the urgent process is performed. Specifically, as illustrated in FIG. 6, an error message indicating that a switching preparation to the manual driving is insufficient, and the vehicle is entering an evacuation area is superimposed on the map and displayed on the display device 2. Further, a position of the evacuation area that is a safe area to which the vehicle is retreated is emphasized on the map and displayed on the display device 2. As Information on the position of the evacuation area, for example, the information previously recorded in the road shape data may be used. At the same time, the vehicle moves to the evacuation area, and stops in the evacuation area by the self-driving. Upon a detection that the vehicle is moved to the evacuation area and stops, the driving mode is switched from the self-driving to the manual driving. When the evacuation area does not fall within a predetermined distance (for example, 500 m) from the current position, the vehicle automatically moves to a safe place such as a roadside by the self-driving. With the above configuration, the urgent process in S165 is ended, and thereafter the process in FIG. 3 is ended.

In S170, the self-driving calibration is performed. In the self-driving calibration, a fluctuation and a stability of the control content of the self-travelling control unit 133 in the self-driving are confirmed on the basis of data in a period where the self-driving is performed in the driver characteristic information. Further, states of the sensors 7 and 8 used in the self-driving (to be surely operated or not) is checked. It is also calculated how a control precision of the self-driving fluctuates according to a change in the travel environment such as the road environment and weather.

Subsequently, in S172, a travel locus of the vehicle when the self-driving is performed is predictively calculated on the basis of the states of the sensors 7 and 8, and the control precision measurement result, and a deviance of the resultant locus from an ideal locus is calculated. Incidentally, the ideal locus of the vehicle is a locus when the vehicle travels on a center of a specific lane at a speed lower than a speed limit by a predetermined value or lower, on the basis of the road shape database.

Subsequently, in S175, it is determined whether a continuous self-driving is allowed or not. When the control is advanced from S172 to S175, it is determined whether the self-driving can be continued or not, according to whether the deviance calculated in S172 is smaller than a predetermined reference value or not. In other words, when the deviance is smaller than the reference value, it is determined that the self-driving can be continued, and when the deviance is equal to or larger than the reference value, it is determined that the self-driving cannot be continued. When the control is advanced from S135 to S175, it is determined whether the self-driving can be continued or not, in the same method as that of S155. When it is determined that the self-driving can be continued, the process proceeds to S180, and when it is determined that the self-driving cannot be continued, the process proceeds to S185.

In S180, from the viewpoint of the vehicle state, it is determined whether the continuation of the self-driving is allowed or not. For example, when the control is advanced from S170 to S175, it is determined whether the continuation of the self-driving is allowed or not, on the basis of the result of the self-driving calibration in S170 (whether abnormality is present in the sensor or not). When the control is advanced from S135 to S175, it is determined whether the continuation of the self-driving is allowed or not, on the basis of the result of the self-driving calibration performed lastly in the past.

When it is determined that the self-driving can be continued in S180, the process returns to S110. As a result, the switching of the driving mode is prohibited, and the same driving mode (in this case, the manual driving) is continued even if the vehicle travels over the above-mentioned driving mode switching position.

In this situation, the driver may be notified, by the display device 2, that the self-driving is continued. On the other hand, when it is determined that the self-driving cannot be continued in S180, since it is essential to switch the driving mode to the manual driving, the process proceeds to S185, an urgent process similar to the one executed in S165 is executed, and thereafter the process in FIG. 3 is ended.

The following will describe details of the manual driving calibration in S130. The driving switching unit 135 first executes process in S210 to S230 by multiple times (for example, nine times) in a predetermined time period (for example, for 1 second) in the manual driving calibration.

First, in S210, the current traveling direction and the traveling position of the vehicle are acquired. Subsequently, in S215, the information on the road traffic information (congestion degree of the road, weather) of the recommended route including the current position of the vehicle is received from the transmission device (for example, VICS beacon) disposed outside of the vehicle.

Subsequently, in S220, the information (radius of curvature of a curve, gradient, width, the number of lanes, road surface conditions, and so on) on the current position of the vehicle and the characteristic of the road including the current position is acquired. The information is acquired from the road shape data.

Subsequently in S225, data corresponding to the above items (1) to (18) in the current driving state information at the current position of the vehicle is acquired. Those pieces of information are acquired from the sensors of the vehicle (for example, accelerator sensor 3, brake sensor 4, steering sensor 5, radar 7, camera 8, acceleration sensor not illustrated, and so on).

Subsequently, in S230, at the current point, the information on the degree of driver's uneasiness, which is specified by the physical state detection unit 132 on the basis of the detection result of the electroencephalogram sensors 6, is acquired. In this example, since the driver has already responded to switch the driving mode from the self-driving to the manual driving, the degree of uneasiness acquired in this situation is indicative of the degree of uneasiness in taking over the driving from the current self-driving state.

Further, in S230, the driving switching unit 135 may acquire the degree of driving concentration of the driver. In that case, the degree of driving concentration is specified by the physical state detection unit 132 on the basis of the electroencephalogram detected by the electroencephalogram sensors 6. Also, when the onboard system 100 has a driver camera (not illustrated) that images an occupant's face, the physical state detection unit 132 may specify a sight direction of the driver on the basis of an image of the driver's face captured by the driver camera, and specify the degree of driving concentration of the driver with the use of the specified sight direction.

The data acquired in S210 to S230 is data of the parameters of the traveling state already described. When the repetitive process in S210 to S230 has been ended, in subsequent S235, it is determined whether the current driver has traveled the current position in the past, on the basis of the driver characteristic information in the storage unit 130. When it is determined that the current driver has traveled the position in the past, the process proceeds to S240, and when it is determined that the drive has not traveled the position in the past, the process proceeds to S245.

In S240, a change amount in the degree of uneasiness when the current driver has traveled a road (hereinafter referred to as "switching preparation route") extending from the current position to the driving mode switching position along the recommended route is predicted on the basis of the driver characteristic information recorded in the storage unit 130.

Specifically, when the same driver as the current driver travels on each position of the switching preparation route, the traveling state category is specified based on the driver characteristic information stored in the storage unit 130 at each position of the switching preparation route. Further, when the same driver as the current driver travels on the same position, the degree of driver's uneasiness is specified on the basis of the emotion correlation data 130b of the same driver stored in the storage unit 130. Incidentally, when multiple different degrees of uneasiness are specified at the same position, the representative value (for example, mean value, median) of the degrees of uneasiness may be set as the degree of uneasiness at the same position. Incidentally, in the process of S240, the traveling state category to be used may be limited to only the traveling state category when the self-driving is performed. Alternatively, both of the traveling state categories when the self-driving is performed and when the manual driving is performed may be used.

With the above process, the past degree of uneasiness at each point in the switching preparation route is specified. In S240, a relative change amount in the past degree of driver's uneasiness at each point in the switching preparation route with reference to the past degree of driver's uneasiness at the current position is obtained on the basis of the above information.

Subsequently, in S245, it is determined whether the degree of uneasiness exceeds a predetermined threshold or not, that is, whether the driver's uneasiness is intense over a certain reference level or not.

Specifically, when the control is advanced directly from S235 to S245 while bypassing S240, a representative value (for example, mean value, median) of the multiple degrees of uneasiness acquired in previous S230 is calculated, and it is determined whether the representative value exceeds a predetermined threshold or not.

When the control is advanced from S240 to S245, a representative value (for example, mean value, median) of the multiple degrees of uneasiness acquired in previous S230 is calculated, and a relative change amount acquired in S240 is further applied to the representative value. With the above process, an estimation value of the degree of uneasiness at each position of the switching preparation route is calculated. It is determined whether a representative value of the estimation values (for example, mean value, maximum value, minimum value, medium) exceeds the above threshold or not.

When it is determined that the representative value does not exceed the threshold, the process proceeds to S250, and it is determined that the driving mode can be switched to the manual driving. When it is determined that the representative value exceeds the threshold, the process proceeds to S260, and it is determined that the driving mode cannot be switched to the manual driving. After S250 and S260, the manual driving calibration is ended, and the process returns to S135 in FIG. 3.

With the above configuration, when the current degree of driver's uneasiness is high or when it is predicted that the degree of driver's uneasiness will become high along the preparation route, it is determined that a change from the self-driving to the manual driving cannot be performed. In that case, the vehicle control coping with the degree of driver's uneasiness is performed. Specifically, when the continuous self-driving is allowed, the self-driving is carried out. When the continuous self-driving is not allowed, the vehicle is stopped in an evacuation area.

When the current degree of driver's uneasiness is low or when it is predicted that the degree of driver's uneasiness does not become high along the preparation route, the driving mode is switched from the self-driving to the manual driving at the driving mode switching position or in the vicinity of the driving mode switching position.

Figure 8:
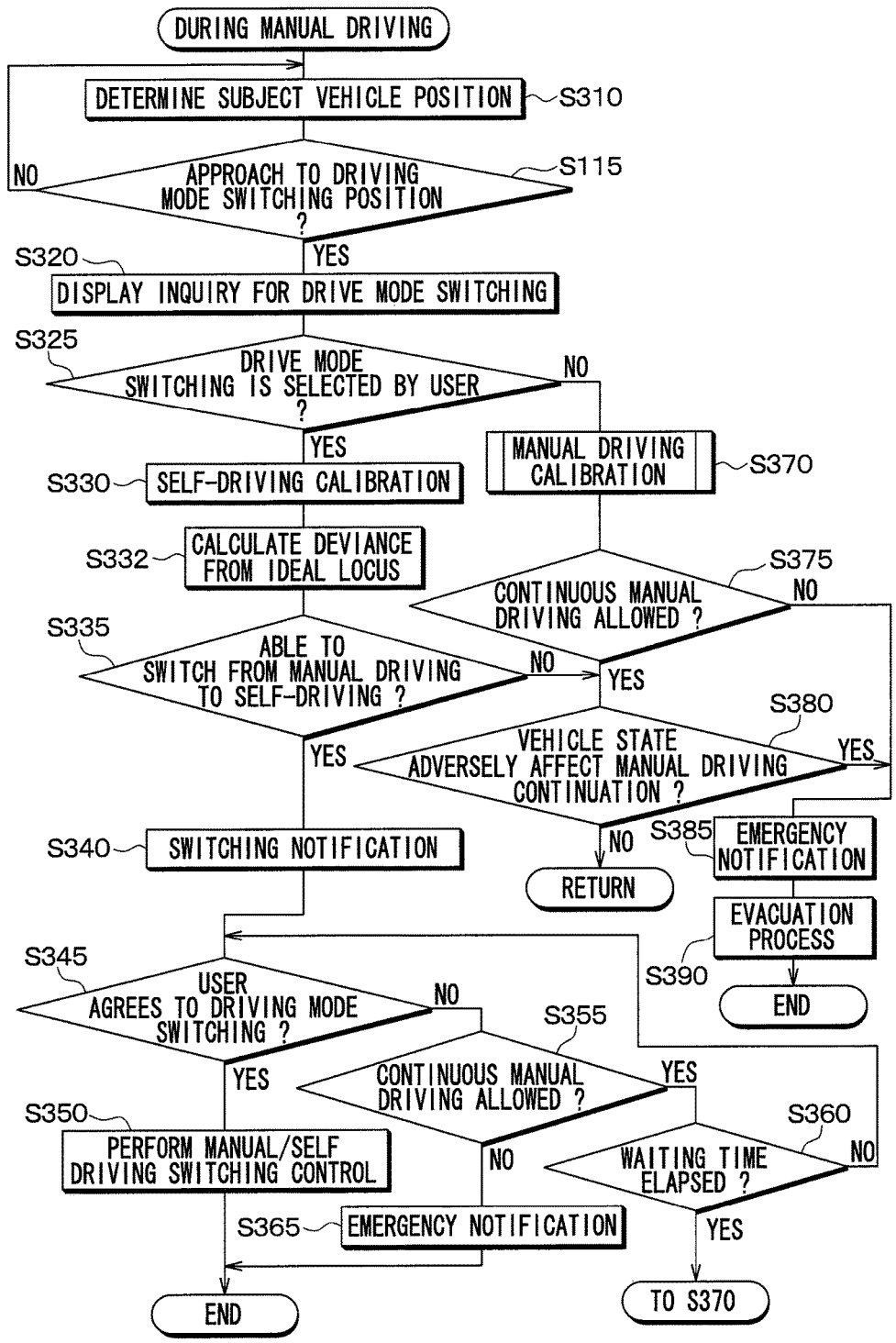
FIG. 8 is a flowchart of operation executed by a driving switching unit during a manual driving.

The following will describe the operation performed by the driving switching unit 135 during the manual driving of the vehicle with reference to FIG. 8. During the manual driving, first in S310, the driving switching unit 135 specifies the current position of the subject vehicle. Subsequently, in S315, it is determined whether the vehicle enters an area distanced from a driving mode switching position where the manual driving mode switches to the self-driving mode within a predetermined range (for example, 5 km) along the recommended route in a traveling direction. That is, it is determined that whether the vehicle approaches the driving mode switching position within the predetermined range.

For example, a boundary point between the manual driving dedicated road and the self-driving dedicated road may be defined as the driving mode switching position where the driving mode switches from the manual driving mode to the self-driving mode. For example, a boundary point between the manual driving dedicated road and the self-driving priority road may be defined as the driving mode switching position where the driving modes switches from the manual driving mode to the self-driving mode. Until it is determined that the driving mode switching position approaches the area within the predetermined distance in S315, the process in S310 and S315 is repeated. When it is determined that the vehicles approaches the driving mode switching position within the predetermined range, the process then proceeds to S320.

In S320, the driver is notified of the fact that the vehicle approaches the driving mode switching position by the display device 2, and the driver is asked whether to switch to the manual driving or not, by the display device 2.

For example, a display in which "during self-driving" in FIG. 4 is displayed by changing "during self-driving" to "during manual driving" on the display device 2. In other words, the current position, the recommended route, and the driving mode switching position are superimposed on the map, and the image on which a message indicating that the vehicle is in the manual driving, and approaches the driving mode switching position is further superimposed is displayed on the display device 2. Further, as illustrated in FIG. 4, a message inquiring about whether to switch the driving mode or not, is superimposed on the map in the display device 2. In response to the inquiry, the driver operates an operation device (for example, touch panel, button) not illustrated, or the like, to answer for whether to switch the driving mode or not.

Subsequently, in S325, it is determined whether the driver's answer to the inquiry in S320 is to switch the driving mode or not to switch the driving mode. When it is determined that the answer is to switch the driving mode, the process proceeds to S330, and when it is determined that the answer is not to switch the driving mode, the process proceeds to S370.

Figure 3:
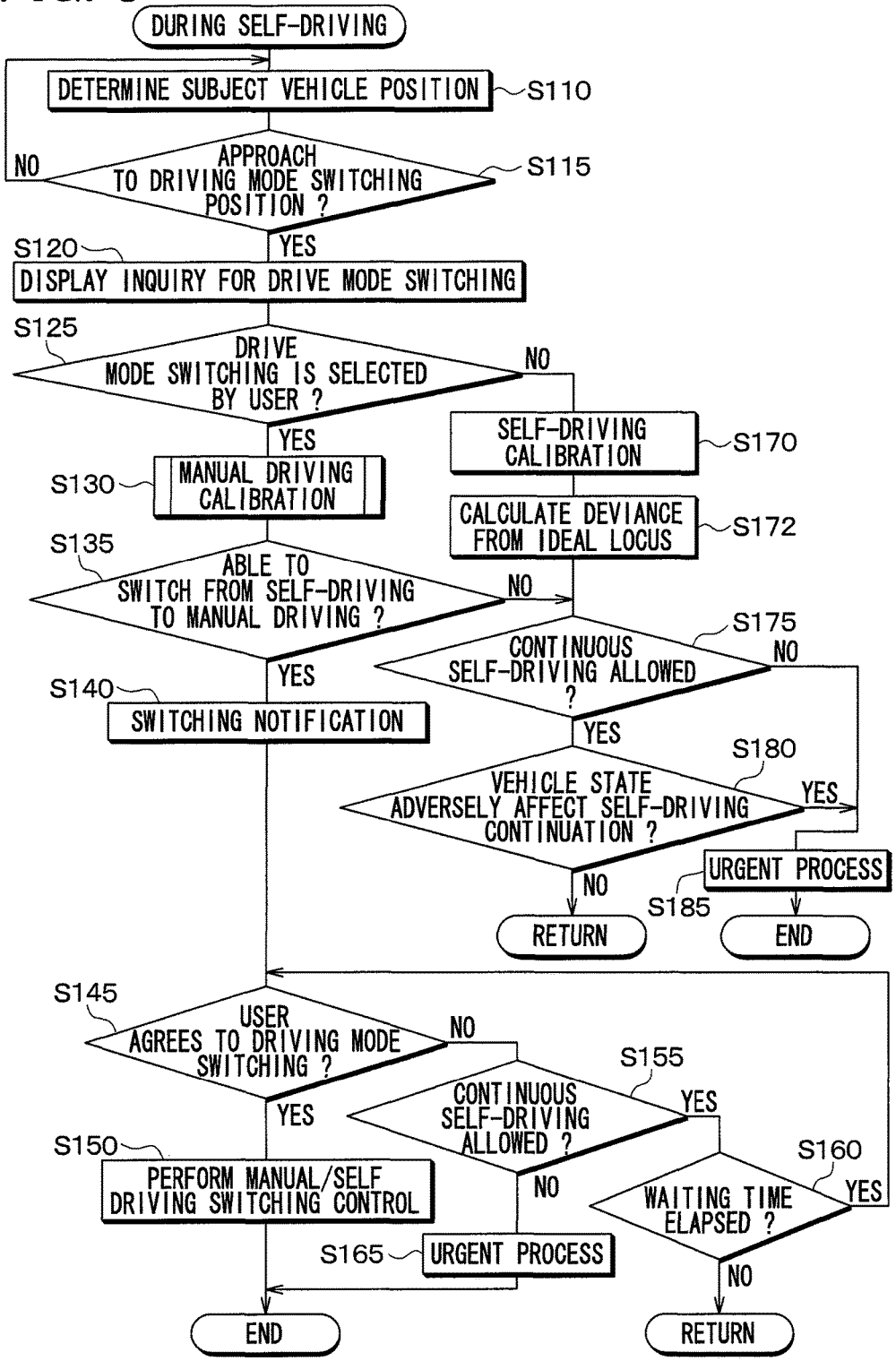
FIG. 3 is a flowchart of an operation executed by a driving switching unit during a self-driving.

In S330, the self-driving calibration is executed in the same method as that in S170 of FIG. 3. Subsequently, in S332, the deviance is calculated in the same method as that in S172.

Subsequently in S335, it is determined whether the self-driving can be continued or not, according to whether the deviance calculated in S332 is smaller than a predetermined reference value or not. In other words, when the deviance is smaller than the reference value, it is determined that the self-driving can be continued, and when the deviance is equal to or larger than the reference value, it is determined that the self-driving cannot be continued. When it is determined that the self-driving can be continued, the process proceeds to S340, and when it is determined that the self-driving cannot be continued, the process proceeds to S380.

In S340, the driving mode switching notification is performed. Specifically, a notification that the driving mode is to be switched to the self-driving at the driving mode switching position is performed by the display device 2. Subsequently, in S345, it is determined whether the driver agrees to the driving mode switching by making an operation in response to the notification in S340 on the operation device which is not illustrated. When it is determined that the approval operation is performed, the process proceeds to S350, and when it is determined that the approval operation is not performed, the process proceeds to S355.

In S350, at a time when the vehicle arrives at the driving mode switching position, or at a time a little earlier than the arrival time (for example, 10 seconds prior to the arrival time), a manual/self driving switching control is performed. In other words, the vehicle is switched from the manual driving to the self-driving. In this situation, in a display shown in FIG. 5, "manual driving" is replaced with "self-driving". In other words, a message indicating that the driving mode is switched from the manual driving driving to the self-driving is superimposed on the map, and displayed on the display device 2. After S350, the process in FIG. 8 is ended.

In S355, it is determined whether the current driving mode (in this case, manual driving) can be continued or not, after passing the driving mode switching position along the recommended route. For example, when the self-driving category of the road after passing the driving mode switching position along the recommended route is the self-driving priority road, it is determined that the current driving mode can be continued, and the process proceeds to S360. For example, when the self-driving category of the road after passing the driving mode switching position along the recommended route is the self-driving dedicated road, it is determined that the current driving mode cannot be continued, and the process proceeds to S365.

In S360, it is determined whether an elapsed time after the notification is performed in S340 reaches a predetermined waiting time (for example, 1 minute). When the elapsed time does not reach the predetermined waiting time, the process returns to S345. When the elapsed time reaches the predetermined waiting time, the process proceeds to S370 while the manual driving is continued.

Figure 9:
FIG. 9 is a diagram illustrating a message inquiring about a route change.

In S365, an emergency notification is performed. Specifically, a notification indicating that the manual driving mode cannot be continued is notified to the driver. For example, as illustrated in FIG. 9, a message of "Approaching toward a self-driving dedicated road.", and an inquiry message to promote a route change are superimposed on the map, and displayed on the display device 2 for a predetermined time. When the driver performs the operation of approval for the inquiry message on the operation device which is not illustrated, the driver characteristic recording unit 134 causes the above-mentioned car navigation apparatus to change the recommended route. After S365, the process in FIG. 8 is ended.

Figure 7:
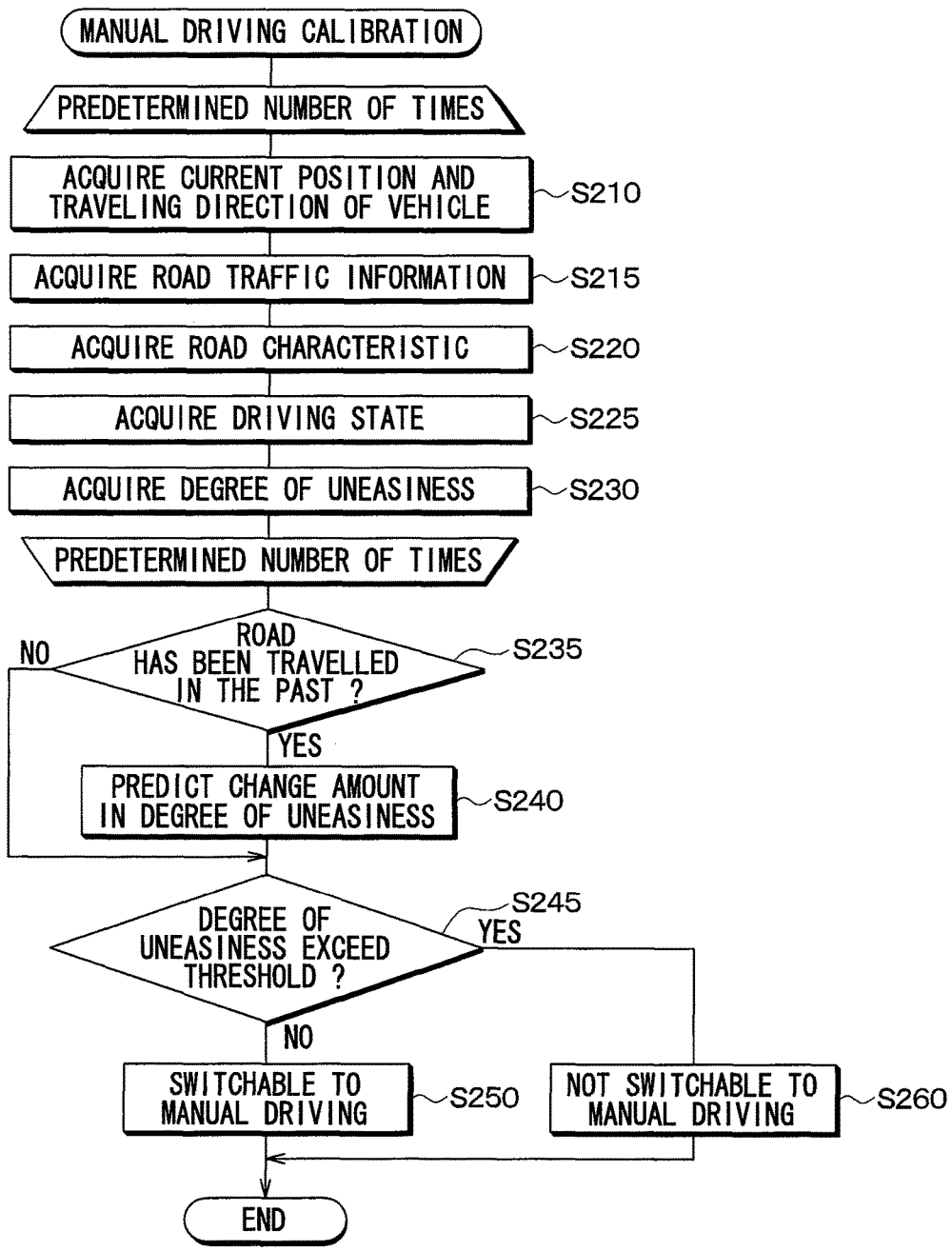
FIG. 7 is a flowchart of a manual driving calibration.

In S370, the manual driving calibration is executed. In the manual driving calibration performed in this situation, it is determined whether the manual driving is enabled or not, on the basis of the degree of driver's uneasiness, or the like. Specifically, the same process as that in FIG. 7 is performed. However, the degree of uneasiness acquired in S230 is indicative of the degree of uneasiness in continuing the self-driving since the driver has already responded to continue the manual driving. Thus, in S250, it is determined that the manual driving can be continued. In S260, it is determined that the manual driving cannot be continued.

Subsequently, in S375, it is determined whether the manual driving can be continued or not, on the basis of the result in S370. When it is determined that there is no abnormality in S370, it is determined that the manual driving can be continued, and the process proceeds to S380. When it is determined that there exists abnormality, it is determined that the manual driving cannot be continued, and the process proceeds to S385.

In S380, whether the continuation of the manual driving is allowed is determined based on whether the vehicle state adversely affects the manual driving, and is displayed by the display device 2. It is determined whether the continuation of the manual driving is allowed or not on the basis of the result of the driver's answer to the inquiry with the use of the operation device. When it is determined that the continuation of the manual driving is not allowed, the process proceeds to S385. When it is determined that continuation of the manual driving is allowed, the manual driving is continued, and the process returns to S310. As an example in which the vehicle state adversely affects the manual driving may be a case where, for example, the driver has a bad physical condition for driving the vehicle.

In S385, a fact that the manual driving cannot be continued is notified to the occupant by the display device 2. When the driver has input a problematic condition of the driver with the use of the operation device, the driver notifies the occupant of the problematic condition.

Subsequently, in S390, the evacuation process is performed. Specifically, an error message indicating that the vehicle is moved to the evacuation area is superimposed on the map and displayed on the display device 2. Further, a position of the evacuation area that is a safe area to which the vehicle is retreated is emphasized on the map and displayed on the display device 2. As Information on the position of the evacuation area, for example, the information previously recorded in the road shape data may be used. At the same time, the vehicle is moved to the evacuation area, and stopped in the evacuation area by the self-driving. Upon a detection that the vehicle is moved to the evacuation area and made a stop, the driving mode is switched from the self-driving to the manual driving. After S390, the process in FIG. 8 is ended.

In the present embodiment, the process performed in S130, S135, S375, and S380 by the driving switching unit 135 function as a determination unit, and the process performed in S175, S180, S185, S380, S385, and S390 by the driving switching unit 135 functions as an uneasiness coping unit.

Other Embodiments

The present disclosure is not limited to the above embodiment, but can appropriately change within a scope of the claims. Further, in the embodiments described above, it goes without saying that the components are not always indispensable unless otherwise clearly stated or except the case where the components are clearly indispensable in principle. In the above-described embodiments, when a numerical value of the number, the numerical value, the quantity, the range, and the like of a configuration element of the embodiment are mentioned, the numerical value is not limited to the specified number excluding a case where it is clearly stated to be particularly essential and a case where it is obviously limited to the specified number in principle. In the above-described embodiments, when a shape, a positional relationship, and the like of a configuration element and the like are mentioned, the shape, the positional relationship, and the like are not limited thereto excluding a particularly stated case and a case of being limited to specific shape, positional relationship, and the like based on the principle. The present disclosure permits the following modification examples with respect to the above-described embodiments. The following modification examples are independently capable of selecting whether to be applied or not applied to the above-described embodiments. In other words, an arbitrary combination of the following modification examples is capable of being applied to the above-described embodiments.

(Modification 1)

In the above embodiment, when the degree of driver's uneasiness about the switching to the manual driving exceeds the threshold during the self-driving, the self-driving is continued (S135 in FIG. 3).

The configuration may not be always limited to the above configuration. From the viewpoint that the degree of driver's uneasiness about the switching to the manual driving is high because the control content by the self-driving does not match the driver, it is conceivable that another coping may be performed. In other words, when the degree of driver's uneasiness about the switching to the manual driving exceeds the threshold, another vehicle control coping with the degree of driver's uneasiness may be performed.

For example, when the degree of driver's uneasiness about the switching to the manual driving exceeds the threshold during the self-driving, the control content by the self-driving may be changed to another content of self-driving easily accepted by the driver.

Specifically, the control content of the self-driving may be changed to obtain a travel pattern close to a safe travel experienced by the driver up to then. In order to achieve the above, a record of the control content of the vehicle during the past travel (during self-driving or manual driving) where the driver has not strongly felt uneasy is extracted, and the control content of the self-driving may be changed so as to approach the extracted control content.

For example, it is assumed that when the vehicle is descending a slope at a speed of 50 km/h in the self-driving mode, the driving switching unit 135 determines that the vehicle approaches the driving mode switching position in S115 of FIG. 3, and determines that there is a reply for switching the driving mode in S125. It is assumed that the driver has a habit of reducing the vehicle speed down to 40 km/h or lower in the downstream of the slope.

In that case, the driving switching unit 135 determines that the degree of uneasiness exceeds the threshold in S245 of FIG. 7 in the manual driving calibration of S130. As a result, the driving switching unit 135 determines that the driving mode cannot be switched to the manual driving in S135 of FIG. 3. However, in this example, the control does not proceed to S175, but the control content of the self-driving may be changed, and the vehicle speed is reduced to a speed V of 40 km/h or lower. Then, the process proceeds to S140.

As described above, after decelerating to a speed with which the driver becomes familiar regularly by the self-driving, and then switches to the manual driving, thereby being capable of reducing the degree of driver's uneasiness to switching of the driving mode.

That the driver has a habit of reducing the vehicle speed down to 40 km/h or lower in the downstream of the slope can be specified on the basis of the driver characteristic information (identification information, physical state information) recorded in the storage unit 130. Specifically, the driving switching unit 135 specifies the degree of uneasiness of the current driver at the time at each past time on the basis of the identification information and the physical state information of the driver.

Then, the driving switching unit 135 extracts the travel content (self-driving or manual driving) at each time when the degree of uneasiness is lower than the predetermined threshold from the driving state information. Further, the driving switching unit 135 calculates a mean value of the vehicle speeds on the road (that is, downhill), a downward slope of which is a predetermined angle or more, on the basis of information on the road characteristic in the extracted information. For example, in the above example, the mean value is a specific speed value V of 40 km/h or lower.

(Modification 2)

In the above embodiment, the vehicle information processing ECU 13 detects the degree of driver's uneasiness on the basis of an output from the electroencephalogram sensors 6 with the use of the electroencephalogram sensors 6 for detecting the electroencephalograms from the multiple positions of the person's (driver's) head.

However, in order to detect the degree of driver's uneasiness, the electroencephalogram sensors 6 may not be always employed. For example, a cerebral blood flow sensor for detecting cerebral blood flow rates from multiple positions of a person's head may be employed. As with the electroencephalograms, an activated portion of the brain can be specified from the cerebral blood flow rate. In other words, the sensor used to detect the degree of driver's uneasiness is configured by any brain activity sensor capable of detecting the activated portion of the brain.

As a measurement method of the electroencephalograms and the cerebral blood flow, a method in which a wearable infrared sensor that comes in contact with the person's head is worn for measurement may be employed. As such an infrared sensor, a near infrared spectoroscopy (NIRS) and an electroencephalograph (EEG) have been known.

In addition, as a measurement method of the electroencephalogram and the cerebral blood flow, a method in which a sensor (for example, sensor shaped into a parabolic antenna) capable of measuring weak electromagnetic waves generated in the brain is installed in a portion above the person (a ceiling portion of the vehicle) for measurement (magnetoencephalography: MEG) may be employed. In this case, in order to measure weak electromagnetic waves generated in the brain, it is necessary to provide a shield for shielding electromagnetic noise reaching a head portion from a portion other than the brain. For that reason, for example, a vehicle interior may be separated from a vehicle power control ECU or a high-frequency communication line, and in detection of the electroencephalogram, a wireless communication device in the vehicle interior may be stopped. The magnetoencephalography can precisely specify current sources of a primary auditory cortex, a primary somatosensory cortex, and a primary motor cortex. Since the magnetoencephalography measures a signal caused by a neural activity directly, a time resolution of the magnetoencephalography is comparable to the measurement by an intracranial electrode.

(Modification 3)

In the above embodiment, the vehicle information processing ECU 13 performs the vehicle control coping with the degree of driver's uneasiness after the driver answers with the intention that the driving mode is switched from the self-driving to the manual driving, and after the driver answers with the intention that the driving mode is not switched from the manual driving to the self-driving. Alternatively, for example, after the driver answers with the intention that the driving mode is switched from the manual driving to the self-driving, the vehicle information processing ECU 13 may perform the vehicle control coping with the degree of driver's uneasiness.

(Modification 4)

In the above embodiment, the vehicle information processing ECU 13 switches between the self-control and the manual control of the vehicle. However, when the vehicle information processing ECU 13 can communicate with a remote control server outside of the vehicle, the vehicle information processing ECU 13 may control the braking, driving, and steering of the vehicle on the basis of a remote control command received from the remote control server.

(Modification 5)

In FIG. 3, after S130 and before S135 in FIG. 3, the driving switching unit 135 may specify the load shape of the driving mode switching position on the basis of the road shape database or the like, and may predictively determine whether the road shape of the driving mode switching position is a point at which the driver can switch the driving mode safely or not. It is determined whether a certain road shape is a road shape in which the driver can switch the driving mode safely or not, on the basis of the driver characteristic data. For example, the driver determines the road shape on the basis of a mean speed, the number of brake depressions per unit distance, or the like in the data of the road shape.

In that case, in S135, the driving switching unit 135 determines whether the manual driving is enabled or not, on the basis of both of the determination result in S130 and whether the road shape enables the driver to switch the driving mode safely or not.

(Modification 6)

After S130 and before S135 in FIG. 3, the driving switching unit 135 may specify the content of the driver's manual driving of the day on the basis of the driver characteristic data, and calculate a deviance between the content of the user's manual driving result and the content of the ideal safe driving. The content of the ideal safe driving may be set to a content in which the vehicle travels on the center of a specific lane, for example, at a speed of 80% of a speed limit.

In that case, in S135, the driving switching unit 135 determines whether the manual driving is enabled or not, on the basis of both of the determination result of S130 and the above-mentioned deviance.

(Modification 7)

In the above embodiment, it is determined in what kind of state the driver is while the driver is driving the vehicle safely, on the basis of the distribution and the degree of activity of the activated portion of the brain. The frontal cortex and the visual cortex in the brain which govern the preference and judgment of the driver are activated during the driving. The activity of the frontal cortex and the visual cortex is small when the driving is stable.

On the other hand, when the vehicle situation is largely changed, or when a large change of the vehicle situation can be predicted (current driving mode switching), the active area of the brain is changed.

When the driving mode is switched from the manual driving to the self-driving and there is an uneasiness about the switching, portions hatched by dots in FIG. 2A are activated. The vehicle information processing ECU 13 measures the active state at each portion of the brain regularly on the basis of the detection results of the electroencephalogram sensors 6, and guesses the driver's emotion according to change of the active state in the method already described.

Further, the vehicle information processing ECU 13 may perform a stabilization control, for example, after the driver answers with an intention that the driving mode is switched from the self-driving to the manual driving, after the driver answers with an intention that the driving mode is not switched from the manual driving to the self-driving, and after the driver answers with an intention that the driving mode is switched from the manual driving to the self-driving.

In the stabilization control, when the vehicle information processing ECU 13 detects that the driver's emotion is changed from an uneasy state (a state of FIG. 2A) to a fear state (a state of FIG. 2B), on the basis of a measurement result of the active area of the brain, the vehicle information processing ECU 13 performs a process for reducing the driver's uneasiness.

For example, an image or sound for forgetting that the driving mode is the self-driving may be presented to the driver. Further, canceling sounds for muting a sound of the vehicle which is generated during the self-driving (for example anti-phase sound of the vehicle sound) may be output from speakers arranged in multiple positions in the vehicle.

Also, in the stabilization control, when the vehicle information processing ECU 13 detects that the driver has an anger emotion (FIG. 2C) on the basis of the measurement result of the active area of the brain, the vehicle information processing ECU 13 may perform a control to suppress the user's anger and allow the driver to enjoy the vehicle travel. For example, a sound and an image may be presented to the driver, a vehicle interior temperature may be changed with the use of an air conditioning apparatus, or fragrance for stabilizing the emotion may be presented to the driver and the occupant with the use of an odor generation device.

A control method for controlling the switching between the manual driving and the self-driving as the driving mode of the vehicle according to the above embodiment and the modifications may be provided as a program or a program product stored in a computer-readable non-transitory tangible storage medium.

While the disclosure has been described with reference to preferred embodiments thereof, it is to be understood that the disclosure is not limited to the preferred embodiments and constructions. The disclosure is intended to cover various modification and equivalent arrangements. In addition, the various combinations and configurations, which are preferred, other combinations and configurations, including more, less or only a single element, are also within the spirit and scope of the disclosure.

The invention claimed is:

1. An onboard system equipped to a vehicle comprising:
a vehicle control device controlling a switching of a driving mode of the vehicle between a manual driving and a self-driving; and
a brain activity sensor capable of detecting an activated portion of a brain of a driver of the vehicle, wherein
the vehicle control device determines whether a degree of uneasiness felt by the driver exceeds a threshold or not based on a detection result detected by the brain activity sensor before the switching of the driving mode,
when determining that the degree of uneasiness felt by the driver does not exceed the threshold, the vehicle control device switches the driving mode,
when determining that the degree of uneasiness felt by the driver exceeds the threshold, the vehicle control device performs a vehicle control corresponding to the degree of uneasiness felt by the driver, and
when determining that the degree of uneasiness felt by the driver exceeds the threshold, the vehicle control device forbids the switching of the driving mode as the vehicle control corresponding to the degree of uneasiness felt by the driver.

2. The onboard system according to claim 1, wherein the vehicle control device includes:
a storage unit storing a brain emotion map indicative of a relation between a distribution of the activated portion of the brain of the driver and the degree of uneasiness felt by the driver; and
a driving switching unit applying, to the brain emotion map, the distribution of the activated portion of the brain which is generated based on the detection result of the brain activity sensor to specify the degree of uneasiness felt by the driver, and the driving switching unit determines whether the degree of uneasiness that is specified exceeds the threshold or not.

3. The onboard system according to claim 1, wherein, after the driver gives an answer to switch the driving mode from the self-driving to the manual driving in response to an inquiry about the driving mode, the vehicle control device forbids the switching of the driving mode when determining that the degree of uneasiness felt by the driver exceeds the threshold.

4. The onboard system according to claim 1, wherein, after the driver gives an answer not to switch the driving mode from the manual driving to the self-driving in response to an inquiry about the driving mode, the vehicle control device notifies the driver that the manual driving cannot be continued when determining that the degree of uneasiness felt by the driver exceeds the threshold.

5. A vehicle control device for controlling a switching of a driving mode of a vehicle between a manual driving and a self-driving, the vehicle control device comprising:
a determination unit determining whether a degree of uneasiness felt by a driver of the vehicle exceeds a threshold or not based on a detection result of a brain activity sensor, wherein the brain activity sensor is capable of detecting an activated portion of a brain of the driver of the vehicle before the switching of the driving mode; and
an uneasiness coping unit switching the driving mode when the determination unit determines that the degree of uneasiness felt by the driver does not exceed the threshold, wherein the uneasiness coping unit performs a vehicle control corresponding to the degree of uneasiness felt by the driver when the determination unit determines that the degree of uneasiness felt by the driver exceeds the threshold, and
when the determination unit determines that the degree of uneasiness felt by the driver exceeds the threshold, the uneasiness coping unit forbids the switching of the driving mode as the vehicle control corresponding to the degree of uneasiness felt by the driver.

6. A program product stored in a computer-readable non-transitory tangible storage medium, the program product comprising instructions to be executed by a computer, the program product being used for a vehicle control device for controlling a switching of a driving mode of a vehicle between a manual driving and a self-driving, the instructions for implementing:
determining whether a degree of uneasiness felt by a driver of the vehicle exceeds a threshold or not based on a detection result of a brain activity sensor, wherein the brain activity sensor is capable of detecting an activated portion of a brain of the driver of the vehicle before the switching of the driving mode;
switching the driving mode when determining that the degree of uneasiness felt by the driver does not exceed the threshold; and
performing a vehicle control corresponding to the degree of uneasiness felt by the driver when determining that the degree of uneasiness felt by the driver exceeds the threshold, wherein
when determining that the degree of uneasiness felt by the driver exceeds the threshold, the switching of the driving mode is forbidden as the vehicle control corresponding to the degree of uneasiness felt by the driver.

7. An onboard system equipped to a vehicle comprising:
a vehicle control device controlling a switching of a driving mode of the vehicle between a manual driving and a self-driving; and
a brain activity sensor capable of detecting an activated portion of a brain of a driver of the vehicle, wherein
the vehicle control device determines whether a degree of uneasiness felt by the driver exceeds a threshold or not based on a detection result detected by the brain activity sensor before the switching of the driving mode,
when determining that the degree of uneasiness felt by the driver does not exceed the threshold, the vehicle control device switches the driving mode,
when determining that the degree of uneasiness felt by the driver exceeds the threshold, the vehicle control device performs a vehicle control corresponding to the degree of uneasiness felt by the driver, and after the driver gives an answer to switch the driving mode from the self-driving to the manual driving in response to an inquiry about the driving mode, the vehicle control device forbids the switching of the driving mode when determining that the degree of uneasiness felt by the driver exceeds the threshold.

8. The onboard system according to claim 7, wherein the vehicle control device includes:

a storage unit storing a brain emotion map indicative of a relation between a distribution of the activated portion of the brain of the driver and the degree of uneasiness felt by the driver; and a driving switching unit applying, to the brain emotion map, the distribution of the activated portion of the brain which is generated based on the detection result of the brain activity sensor to specify the degree of uneasiness felt by the driver, and the driving switching unit determines whether the degree of uneasiness that is specified exceeds the threshold or not.

9. The onboard system according to claim 7, wherein, after the driver gives an answer not to switch the driving mode from the manual driving to the self-driving in response to an inquiry about the driving mode, the vehicle control device notifies the driver that the manual driving cannot be continued when determining that the degree of uneasiness felt by the driver exceeds the threshold.

10. An onboard system equipped to a vehicle comprising:

a vehicle control device controlling a switching of a driving mode of the vehicle between a manual driving and a self-driving; and a brain activity sensor capable of detecting an activated portion of a brain of a driver of the vehicle, wherein the vehicle control device determines whether a degree of uneasiness felt by the driver exceeds a threshold or not based on a detection result detected by the brain activity sensor before the switching of the driving mode, when determining that the degree of uneasiness felt by the driver does not exceed the threshold, the vehicle control device switches the driving mode, when determining that the degree of uneasiness felt by the driver exceeds the threshold, the vehicle control device performs a vehicle control corresponding to the degree of uneasiness felt by the driver, and after the driver gives an answer not to switch the driving mode from the manual driving to the self-driving in response to an inquiry about the driving mode, the vehicle control device notifies the driver that the manual driving cannot be continued when determining that the degree of uneasiness felt by the driver exceeds the threshold.

11. The onboard system according to claim 10, wherein the vehicle control device includes:

a storage unit storing a brain emotion map indicative of a relation between a distribution of the activated portion of the brain of the driver and the degree of uneasiness felt by the driver; and a driving switching unit applying, to the brain emotion map, the distribution of the activated portion of the brain which is generated based on the detection result of the brain activity sensor to specify the degree of uneasiness felt by the driver, and the driving switching unit determines whether the degree of uneasiness that is specified exceeds the threshold or not.

12. A vehicle control device for controlling a switching of a driving mode of a vehicle between a manual driving and a self-driving, the vehicle control device comprising:

a determination unit determining whether a degree of uneasiness felt by a driver of the vehicle exceeds a threshold or not based on a detection result of a brain activity sensor, wherein the brain activity sensor is capable of detecting an activated portion of a brain of the driver of the vehicle before the switching of the driving mode; and an uneasiness coping unit switching the driving mode when the determination unit determines that the degree of uneasiness felt by the driver does not exceed the threshold, wherein the uneasiness coping unit performs a vehicle control corresponding to the degree of uneasiness felt by the driver when the determination unit determines that the degree of uneasiness felt by the driver exceeds the threshold, and after the driver gives an answer to switch the driving mode from the self-driving to the manual driving in response to an inquiry about the driving mode, the uneasiness coping unit forbids the switching of the driving mode when the determination unit determines that the degree of uneasiness felt by the driver exceeds the threshold.

13. A vehicle control device for controlling a switching of a driving mode of a vehicle between a manual driving and a self-driving, the vehicle control device comprising:

a determination unit determining whether a degree of uneasiness felt by a driver of the vehicle exceeds a threshold or not based on a detection result of a brain activity sensor, wherein the brain activity sensor is capable of detecting an activated portion of a brain of the driver of the vehicle before the switching of the driving mode; and an uneasiness coping unit switching the driving mode when the determination unit determines that the degree of uneasiness felt by the driver does not exceed the threshold, wherein the uneasiness coping unit performs a vehicle control corresponding to the degree of uneasiness felt by the driver when the determination unit determines that the degree of uneasiness felt by the driver exceeds the threshold, and after the driver gives an answer not to switch the driving mode from the manual driving to the self-driving in response to an inquiry about the driving mode, the uneasiness coping unit notifies the driver that the manual driving cannot be continued when the determination unit determines that the degree of uneasiness felt by the driver exceeds the threshold.

14. A program product stored in a computer-readable non-transitory tangible storage medium, the program product comprising instructions to be executed by a computer, the program product being used for a vehicle control device for controlling a switching of a driving mode of a vehicle between a manual driving and a self-driving, the instructions for implementing:

determining whether a degree of uneasiness felt by a driver of the vehicle exceeds a threshold or not based on a detection result of a brain activity sensor, wherein the brain activity sensor is capable of detecting an activated portion of a brain of the driver of the vehicle before the switching of the driving mode;

switching the driving mode when determining that the degree of uneasiness felt by the driver does not exceed the threshold;

performing a vehicle control corresponding to the degree of uneasiness felt by the driver when determining that the degree of uneasiness felt by the driver exceeds the threshold; and after the driver gives an answer to switch the driving mode from the self-driving to the manual driving in response to an inquiry about the driving mode, forbidding the switching of the driving mode when determining that the degree of uneasiness felt by the driver exceeds the threshold.

15. A program product stored in a computer-readable non-transitory tangible storage medium, the program product comprising instructions to be executed by a computer, the program product being used for a vehicle control device for controlling a switching of a driving mode of a vehicle between a manual driving and a self-driving, the instructions for implementing:

determining whether a degree of uneasiness felt by a driver of the vehicle exceeds a threshold or not based on a detection result of a brain activity sensor, wherein the brain activity sensor is capable of detecting an activated portion of a brain of the driver of the vehicle before the switching of the driving mode;

switching the driving mode when determining that the degree of uneasiness felt by the driver does not exceed the threshold;

performing a vehicle control corresponding to the degree of uneasiness felt by the driver when determining that the degree of uneasiness felt by the driver exceeds the threshold; and after the driver gives an answer not to switch the driving mode from the manual driving to the self-driving in response to an inquiry about the driving mode, notifying the driver that the manual driving cannot be continued when determining that the degree of uneasiness felt by the driver exceeds the threshold.

* * * * *